(12) United States Patent
Watanabe et al.

(10) Patent No.: US 6,403,822 B2
(45) Date of Patent: Jun. 11, 2002

(54) ESTER COMPOUNDS HAVING ALICYCLIC STRUCTURE AND METHOD FOR PREPARING SAME

(75) Inventors: Takeru Watanabe; Koji Hasegawa; Takeshi Kinsho; Mutsuo Nakashima; Seiichiro Tachibana; Tsunehiro Nishi; Jun Hatakeyama, all of Nakakubiki-gun (JP)

(73) Assignee: Shin-Etsu Chemical, Co., Ltd. (JP)

( * ) Notice: Subject to any disclaimer, the term of this patent is extended or adjusted under 35 U.S.C. 154(b) by 0 days.

(21) Appl. No.: 09/842,005

(22) Filed: Apr. 26, 2001

(30) Foreign Application Priority Data

Apr. 28, 2000 (JP) ......................................... 2000-131177

(51) Int. Cl.[7] ............................................... C07C 69/74
(52) U.S. Cl. ...................................... 560/116; 560/128
(58) Field of Search ................................... 562/128, 116

(56) References Cited
U.S. PATENT DOCUMENTS 6,063,542 A * 4/1987 Hyeon et al.
6,146,810 A * 9/1998 Seo et al.
6,268,106 B1 * 9/1998 Park et al.

* cited by examiner

Primary Examiner—Gary Geist
Assistant Examiner—Héctor M. Reyes
(74) Attorney, Agent, or Firm—Millen, White, Zelano & Branigan, P.C.

(57) ABSTRACT

Ester compounds of formula (1) are useful as monomers to form base resins for use in chemically amplified resist compositions adapted for micropatterning lithography.

(1)

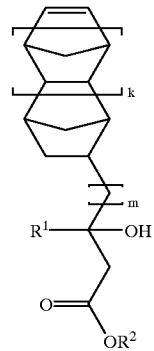

$R^1$ is H or $C_{1-6}$ alkyl, $R^2$ is an acid labile group, k is 0 or 1, and m is an integer from 0 to 5.

14 Claims, No Drawings

ESTER COMPOUNDS HAVING ALICYCLIC STRUCTURE AND METHOD FOR PREPARING SAME

This invention relates to novel ester compounds useful as monomers to form base resins for use in chemically amplified resist compositions adapted for micropatterning lithography, and a method for preparing the same.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 µm or less.

The resist materials for use in photolithography using light of an excimer laser, especially ArF excimer laser having a wavelength of 193 nm, are, of course, required to have a high transmittance to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone an alicyclic compound derived from a norbornene derivative. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing an alicyclic compound in the backbone have rigidity within the acceptable range, but are less reactive with acid than poly(meth)acrylate because of their backbone structure, and difficult to increase reactivity because of the low freedom of polymerization. Additionally, since the backbone is highly hydrophobic, these polymers are less adherent when applied to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel ester compound useful as a monomer to form a polymer for use in the formulation of a photoresist composition which exhibits a high reactivity and substrate affinity when processed by photolithography using light with a wavelength of less than 300 nm, especially ArF excimer laser light as the light source. Another object is to provide a method for preparing the ester compound.

The inventor has found that an ester compound of formula (1) can be prepared in high yields by a simple method and that a resist composition comprising a polymer obtained from this ester compound as a base resin is improved in sensitivity, resolution and substrate adhesion.

The invention provides an ester compound of the following general formula (1).

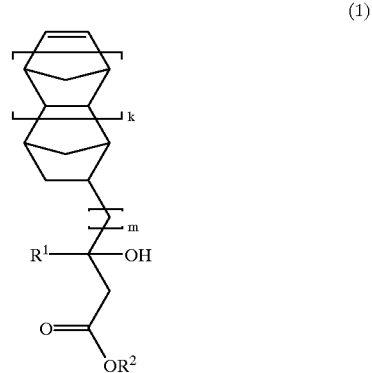

(1)

Herein $R^1$ is hydrogen or a straight, branched or cyclic alkyl group of 1 to 6 carbon atoms, $R^2$ is an acid labile group, k is 0 or 1, and m is an integer from 0 to 5.

Preferably the ester compound has the following general formula (2) or (3).

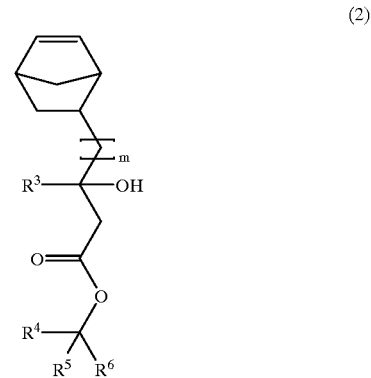

(2)

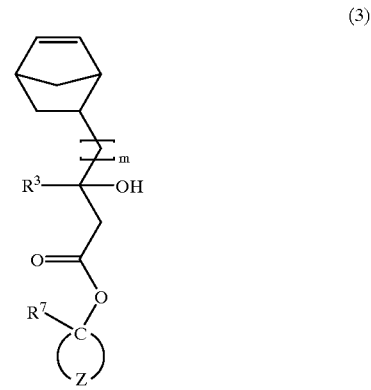

(3)

Herein m is as defined above, $R^3$ is hydrogen or methyl, $R^4$ to $R^7$ are independently selected from straight, branched or cyclic alkyl groups of 1 to 15 carbon atoms, the sum of carbon atoms in $R^4$, $R^5$ and $R^6$ is at least 4, and Z is a divalent hydrocarbon group of 4 to 15 carbon atoms which forms a ring with the carbon atom to which it is connected at both ends.

A method for preparing the ester compound forms another aspect of the invention, which involves the step of effecting addition reaction of a metal enolate of acetate of the following formula (5) to a carbonyl compound of the following formula (4).

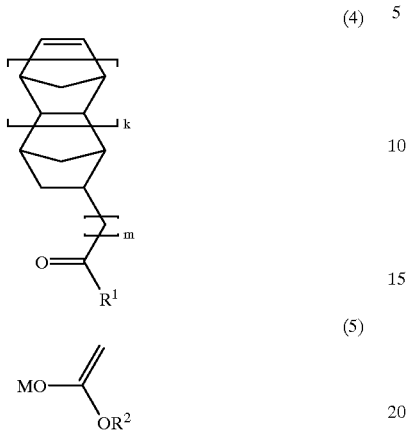

Herein k, m, $R^1$ and $R^2$ are as defined above, M is Li, Na, K, MgY or ZnY, and Y is a halogen atom.

DESCRIPTION OF THE PREFERRED EMBODIMENT

The ester compounds of the invention are of the following general formula (1).

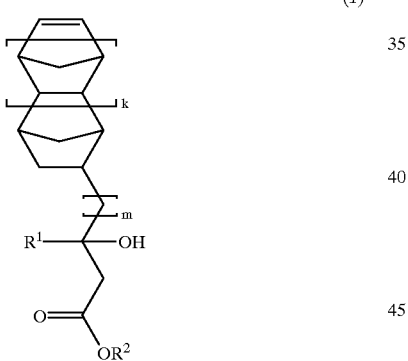

Herein $R^1$ is hydrogen or a straight, branched or cyclic alkyl group of 1 to 6 carbon atoms. Exemplary alkyl groups include methyl, ethyl, propyl, isopropyl, butyl, isobutyl, sec-butyl, tert-butyl, tert-amyl, pentyl, hexyl, cyclopentyl, and cyclohexyl. $R^2$ is an acid labile group. The letter k is 0 or 1, and m is an integer from 0 to 5 (i.e., $0 \leq m \leq 5$), and preferably from 0 to 3.

The preferred acid labile group represented by $R^2$ are those of the following formulas.

$R^4$ to $R^7$ and Z are as defined below.

Preferred among the ester compounds of formula (1) are ester compounds of the following general formula (2) or (3).

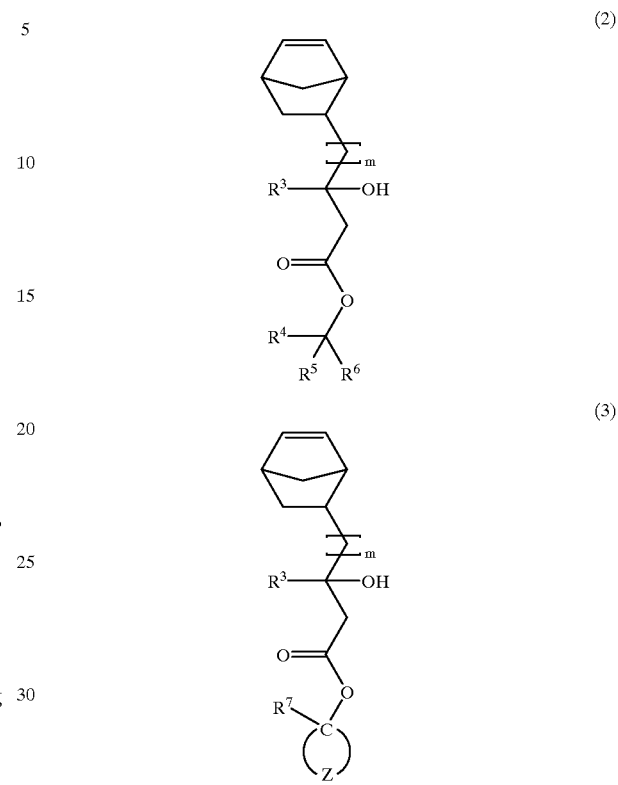

Herein m is as defined above. $R^3$ is hydrogen or methyl. $R^4$ to $R^7$ are independently selected from straight, branched or cyclic alkyl groups of 1 to 15 carbon atoms. The total number of carbon atoms in $R^4$, $R^5$ and $R^6$ is at least 4. Examples of the straight, branched or cyclic alkyl groups of 1 to 15 carbon atoms include methyl, ethyl, propyl, isopropyl, butyl, isobutyl, sec-butyl, tert-butyl, tert-amyl, pentyl, hexyl, cyclopentyl, cyclohexyl, cyclopentylmethyl, cyclopentylethyl, cyclohexylmethyl, cyclohexylethyl, bicyclo[2.2.1]heptyl, bicyclo[2.2.2]octyl, bicyclo[3.3.1]nonyl, bicyclo[4.4.0]decanyl, tricyclo[5.2.1.0$^{2,6}$]decanyl, tetracyclo[4.4.0.1$^{2,5}$.1$^{7,10}$]dodecanyl, and adamantyl. Z stands for divalent hydrocarbon groups of 4 to 15 carbon atoms, such as alkylene and alkenylene groups, which forms a ring with the carbon atom to which it is connected at both ends. Examples of the rings that Z forms include cyclopentane, cyclopentene, cyclohexane, cyclohexene, bicyclo[2.2.1]heptane, bicyclo[4.4.0]decane, tricyclo[5.2.1.0$^{2,6}$]decane, tetracyclo[4.4.0$^{2,5}$.1$^{7,10}$]dodecane, and adamantane.

Illustrative, non-limiting, examples of the ester compounds of formula (1) and formulas (2) and (3) are given below.

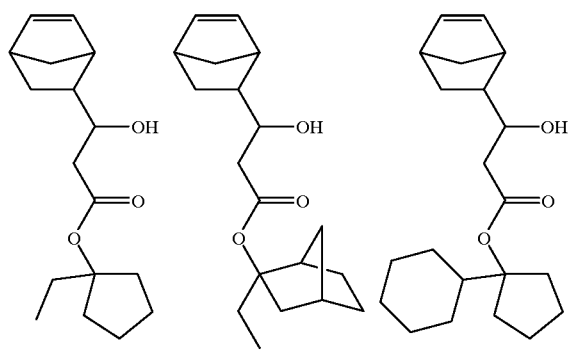
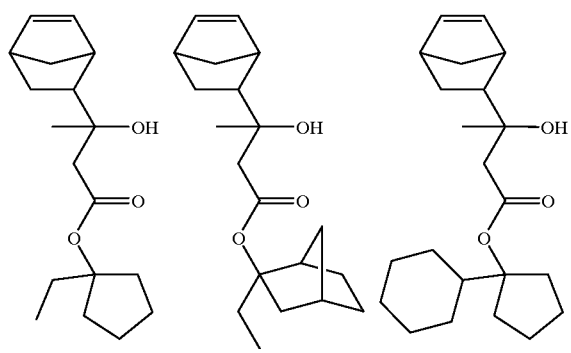
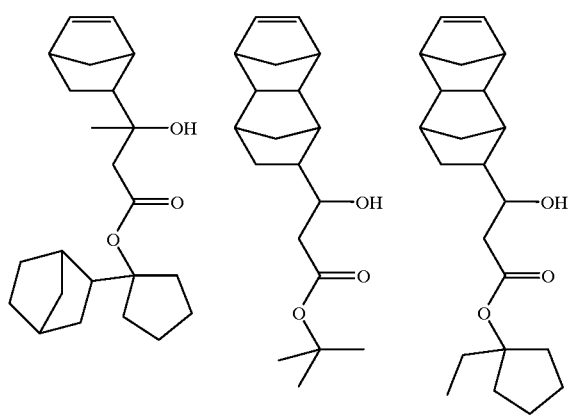
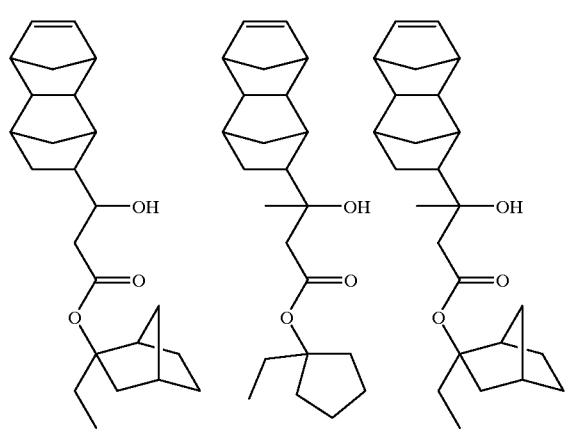
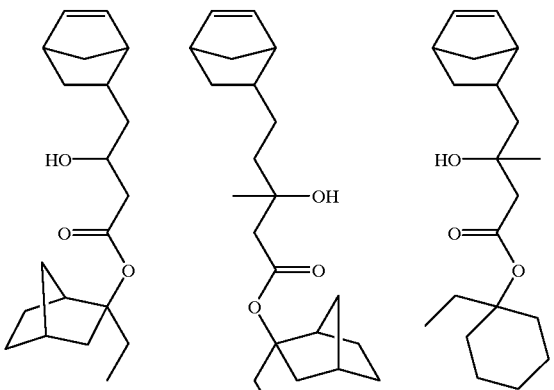
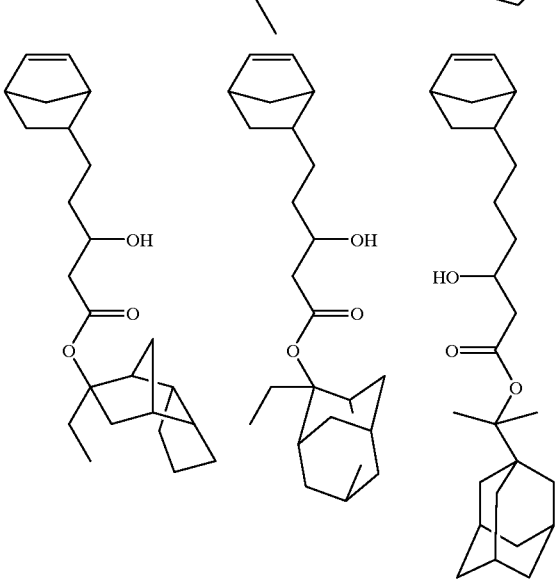
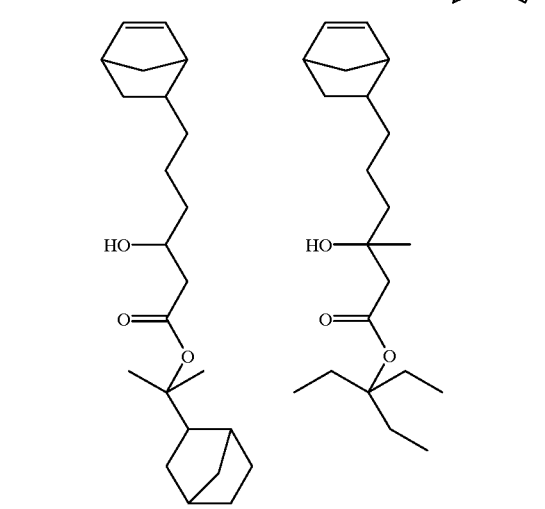

As seen from the reaction scheme shown below, the ester compound of formula (1) can be prepared by the step of causing a base to act on a corresponding acetate of formula (6) (where X is hydrogen) or a corresponding haloacetate of formula (6) (where X is halogen) to form a metal enolate of formula (5) and effecting nucleophilic addition reaction of the metal enolate to a carbonyl compound of formula (4).

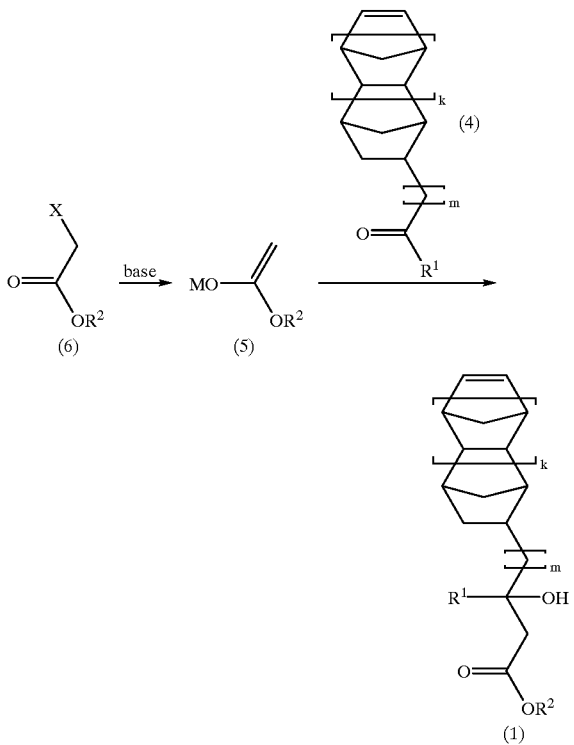

Herein, k, m, $R^1$ and $R^2$ are as defined above. X is hydrogen or halogen. M is Li, Na, K, MgY or ZnY, and Y is halogen.

The bases used for forming the metal enolate include metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide, and bromomagnesium diisopropylamide; alkoxides such as sodium methoxide, sodium ethoxide, lithium methoxide, lithium ethoxide, lithium tert-butoxide, and potassium tert-butoxide; inorganic hydroxides such as sodium hydroxide, lithium hydroxide, potassium hydroxide, barium hydroxide, and tetra-n-butylammonium hydroxide; inorganic carbonates such as sodium carbonate, sodium hydrogen carbonate, lithium carbonate and potassium carbonate; metal hydrides such as boranes, alkylboranes, sodium hydride, lithium hydride, potassium hydride, and calcium hydride; alkyl metal compounds such as trityl lithium, trityl sodium, trityl potassium, methyl lithium, phenyl lithium, sec-butyl lithium, tert-butyl lithium, and ethyl magnesium bromide; and metals such as lithium, sodium, potassium, magnesium, and zinc, but are not limited thereto. It is noted that reaction using haloacetate and zinc is known as Reformatsky reaction.

In the addition reaction of the carbonyl compound of formula (4) with the metal enolate of formula (5), 0.8 to 1.5 mol of the metal enolate is preferably used per mol of the carbonyl compound. Useful solvents are ethers such as tetrahydrofuran, diethyl ether, di-n-butyl ether, 1,4-dioxane, ethylene glycol dimethyl ether, and ethylene glycol diethyl ether and hydrocarbons such as hexane, heptane, benzene, toluene, xylene and cumene, alone or in admixture thereof. The reaction temperature and time vary with particular starting reactants used. In one example where an acetate of formula (6) wherein X is hydrogen and a strong base such as lithium diisopropylamide or lithium bistrimethylsilylamide are used, the preferred reaction conditions include a reaction temperature in the low range of −80° C. to −30° C. and a reaction time of about ½ to 3 hours because the metal enolate is thermally unstable. In another example where a haloacetate of formula (6) wherein X is halogen and a metal such as zinc or magnesium are used, it is generally preferred to keep the reaction temperature in the range of 20 to 80° C. and the reaction time in the range of about 1 to 20 hours. The reaction conditions are not limited to these ranges.

A polymer is prepared using the inventive ester compound as a monomer. The method is generally by mixing the monomer with a solvent, adding a catalyst or polymerization initiator, and effecting polymerization reaction while heating or cooling the system if necessary. This polymerization reaction can be effected in a conventional way.

A resist composition is formulated using as a base resin the polymer resulting from polymerization of the ester compound. Usually, the resist composition is formulated by adding an organic solvent and a photoacid generator to the polymer and if necessary, further adding a crosslinker, a basic compound, a dissolution inhibitor and other additives. Preparation of the resist composition can be effected in a conventional way.

The resist composition formulated using the polymer resulting from polymerization of the inventive ester compound lends itself to micropatterning with electron beams or deep-UV rays since it is sensitive to high-energy radiation and has excellent adhesion to substrates, sensitivity, resolution, and etching resistance. Especially because of the minimized absorption at the exposure wavelength of an ArF or KrF excimer laser, a finely defined pattern having sidewalls perpendicular to the substrate can easily be formed. The resist composition is thus suitable as micropatterning material for VLSI fabrication.

EXAMPLE

Synthesis Examples and Reference Examples are given below for further illustrating the invention. It is not construed that the invention be limited to these examples.

Synthesis Examples are first described. Ester compounds within the scope of the invention were synthesized in accordance with the following procedure.

Synthesis Example 1

Synthesis of 1-ethylcyclopentyl 3-hydroxy-3-(5-norbornen-2-yl)propionate (Monomer 1)

First, in a nitrogen atmosphere, 184 g of lithium bis(trimethylsilyl)amide and 172 g of 1-ethylcyclopentyl acetate were reacted in 1 kg of dry tetrahydrofuran at −60° C. to form lithium enolate. Then 122 g of 5-norbornene-2-carbaldehyde was slowly added, following which the temperature was raised to −20° C. over one hour, at which reaction was effected. Then 1 kg of a saturated ammonium chloride aqueous solution was added to stop the reaction, whereupon hexane was added for extraction. The organic layer was washed with water, dried over anhydrous sodium sulfate, filtered, concentrated in vacuo, and purified by silica gel column chromatography, obtaining 264 g (yield 96%) of 1-ethylcyclopentyl 3-hydroxy-3-(5-norbornen-2-yl) propionate, designated Monomer 1.

IR (thin film): ν=3502 (br.), 3057, 2966, 2870, 1713, 1709, 1335, 1284, 1254, 1167, 1072 cm$^{-1}$

$^1$H-NMR of main diastereomer (270 MHz in CDCl$_3$): δ=0.44 (1H, m), 0.84 (3H, t, J=4.9 Hz), 1.21 (1H, m), 1.41

(1H, m), 1.50–1.80 (7H, m), 1.80–2.20 (5H, m), 2.26 (1H, dd, J=16.6, 9.2 Hz), 2.44 (1H, dd, J=16.6, 2.4 Hz), 2.78 (1H, m), 3.08 (1H, m), 3.27 (1H, m), 3.50 (1H, m), 6.03 (1H, m), 6.13 (1H, m).

Synthesis Example 2

Synthesis of 2-ethyl-2-exo-norbornyl 3-hydroxy-3-(5-norbornen-2-yl)propionate (Monomer 2)

By following the procedure of Synthesis Example 1 except that 2-ethyl-2-exo-norbornyl acetate was used instead of 1-ethylcyclopentyl acetate, there was obtained 2-ethyl-2-exo-norbornyl 3-hydroxy-3-(5-norbornen-2-yl) propionate. Yield 95%.

IR (thin film): ν=3502 (br.), 3057, 2966, 2872, 1722, 1711, 1330, 1193, 1173, 1132, 1074, 1032 cm$^{-1}$ $^1$H-NMR of main diastereomer (270 MHz in CDCl$_3$): δ=0.45 (1H, m), 0.80 (3H, t, J=7.0 Hz), 1.03 (1H, m), 1.10–2.30 {(14H, m) including 2.23 (1H, dd, J=17.0, 7.8 Hz)}, 2.44 (1H, dd, J=17.0, 2.4 Hz), 2.53 (2H, m), 2.78 (1H, m), 3.08 (1H, m), 3.14 (1H, m), 3.26 (1H, m), 6.03 (1H, m), 6.13 (1H, m).

Synthesis Example 3

Synthesis of 1-cyclohexylcyclopentyl 3-hydroxy-3-(5-norbornen-2-yl)propionate (Monomer 3)

By following the procedure of Synthesis Example 1 except that 1-cyclohexylcyclopentyl acetate was used instead of 1-ethylcyclopentyl acetate, there was obtained 1-cyclohexylcyclopentyl 3-hydroxy-3-(5-norbornen-2-yl)-propionate. Yield 94%.

IR (thin film): ν=3496 (br.), 3057, 2931, 2854, 1711, 1448, 1335, 1186, 1155, 1072, 1034 cm$^{-1}$ $^1$H-NMR of main diastereomer (270 MHz in CDCl$_3$): δ=0.45 (1H, m), 0.80–2.15 (23H, m), 2.25 (1H, dd, J=16.5, 9.0 Hz), 2.33 (1H, m), 2.42 (1H, dd, J=16.5, 2.4 Hz), 2.78 (1H, m), 3.07 (1H, m), 3.26 (1H, m), 6.04 (1H, m), 6.13 (1H, m).

Synthesis Example 4

Synthesis of 1-ethylcyclopentyl 3-hydroxy-3-(5-norbornen-2-yl)butyrate (Monomer 4)

By following the procedure of Synthesis Example 1 except that 5-acetyl-2-norbornene was used instead of 5-norbornene-2-carbaldehyde, there was obtained 1-ethylcyclopentyl 3-hydroxy-3-(5-norbornen-2-yl) butyrate. Yield 95%.

IR (thin film): ν=3502 (br.), 3057, 2968, 2873, 1722, 1705, 1459, 1373, 1336, 1211, 1171 cm$^{-1}$ $^1$H-NMR of main diastereomer (270 MHz in CDCl$_3$): δ=0.86 (3H, t, J=7.3 Hz), 1.05 (1H, m), 1.21 (1H, s), 1.37 (1H, m), 1.39 (1H, m), 1.45–2.15 (13H, m), 2.28 (1H, d, J=14.7 Hz), 2.30 (1H, m), 2.37 (1H, d, J=14.7 Hz), 2.70–2.85 (2H, m), 2.91 (1H, m), 6.01 (1H, m), 6.17 (1H, m).

Synthesis Example 5

Synthesis of 2-ethyl-2-exo-norbornyl 3-hydroxy-3-(5-norbornen-2-yl)butyrate (Monomer 5)

By following the procedure of Synthesis Example 4 except that 2-ethyl-2-exo-norbornyl acetate was used instead of 1-ethylcyclopentyl acetate, there was obtained 2-ethyl-2-exo-norbornyl 3-hydroxy-3-(5-norbornen-2-yl) butyrate. Yield 94%.

IR (thin film): ν=3502 (br.), 3057, 2966, 2873, 1704, 1702, 1457, 1373, 1331, 1203, 1173, 1132, 1105 cm$^{-1}$ $^1$H-NMR of main diastereomer (270 MHz in CDCl$_3$): δ=0.82 (3H, t, J=7.6 Hz), 1.00–1.10 (2H, m), 1.15–1.30 {(5H, m) including 1.21 (3H, s)}, 1.30–1.60 (5H, m), 1.65 (1H, m), 1.70–1.90 (2H, m), 1.98 (1H, m), 2.15–2.35 {(4H, m) including 2.28 (1H, d, J=14.6 Hz)}, 2.37 (1H, d, J=14.6 Hz), 2.58 (1H, m), 2.75–2.90 (2H, m), 2.92 (1H, m), 6.01 (1H, m), 6.17 (1H, m).

Synthesis Example 6

Synthesis of 1-cyclohexylcyclopentyl 3-hydroxy-3-(5-norbornen-2-yl)butyrate (Monomer 6)

By following the procedure of Synthesis Example 4 except that 1-cyclohexylcyclopentyl acetate was used instead of 1-ethylcyclopentyl acetate, there was obtained 1-cyclohexylcyclopentyl 3-hydroxy-3-(5-norbornen-2-yl)-butyrate. Yield 95%.

IR (thin film): ν=3502 (br.), 3057, 2933, 2854, 1701, 1699, 1450, 1371, 1336, 1209, 1186, 1157 cm$^{-1}$ $^1$H-NMR of main diastereomer (270 MHz in CDCl$_3$):δ= 0.90–2.05 {(25H, m) including 1.19 (3H, s)}, 2.20–2.40 {(4H, m) including 2.27 (1H, d, J=14.6 Hz), 2.37 (1H, d, J=14.6 Hz)}, 2.79 (1H, m), 2.91 (1H, m), 3.11 (1H, m), 6.00 (1H, m), 6.16 (1H, m).

Synthesis Example 7

Synthesis of 1-(2-norbornyl)cyclopentyl 3-hydroxy-3-(5-norbornen-2-yl)butyrate (Monomer 7)

By following the procedure of Synthesis Example 4 except that 1-(2-norbornyl)cyclopentyl acetate was used instead of 1-ethylcyclopentyl acetate, there was obtained 1-(2-norbornyl)cyclopentyl 3-hydroxy-3-(5-norbornen-2-yl)-butyrate. Yield 92%.

IR (thin film): ν=3502 (br.), 3057, 2954, 2870, 1713, 1454, 1373, 1338, 1207, 1157, 1080 cm$^{-1}$ $^1$H-NMR (270 MHz in CDCl$_3$): δ=0.90–3.05 (32H, m), 5.80–6.35 (2H, m).

Synthesis Example 8

Synthesis of tert-butyl 3-hydroxy-3-(8-tetracyclo-[4.4.0.1$^{2,5}$.1$^{7,10}$]dodecen-3-yl)propionate (Monomer 8)

The procedure of Synthesis Example 1 was repeated except that tert-butyl acetate was used instead of 1-ethylcyclopentyl acetate, and 8-tetracyclo[4.4.0.1$^{2,5}$.1$^{7,10}$]-dodecene-3-carbaldehyde was used instead of 5-norbornene-2-carbaldehyde. There was obtained tert-butyl 3-hydroxy-3-(8-tetracyclo[4.4.0.1$^{2,5}$.1$^{7,10}$]dodecen-3-yl)propionate. Yield 93%.

IR (KBr): ν=3434 (br.), 3049, 2958, 1716, 1394, 1367, 1340, 1313, 1250, 1217, 1151, 1037 cm$^{-1}$ $^1$H-NMR of main diastereomer (270 MHz in CDCl$_3$): δ=0.50–0.70 (2H, m), 0.85 (1H, m), 1.10–2.60 {(19H, m) including 1.44 (9H, s)}, 2.75–3.20 (3H, m), 3.52 (1H, m), 5.85–6.00 (2H, m).

Synthesis Example 9

Synthesis of 1-ethylcyclopentyl 3-hydroxy-3-(8-tetracyclo-[4.4.0.1$^{2,5}$.1$^{7,10}$]dodecen-3-yl)propionate (Monomer 9)

The procedure of Synthesis Example 8 was repeated except that 1-ethylcyclopentyl acetate was used instead of tert-butyl acetate. There was obtained 1-ethylcyclopentyl 3-hydroxy-3-(8-tetracyclo[4.4.0.1$^{2,5}$.1$^{7,10}$]dodecen-3-yl)-propionate. Yield 92%.

IR (thin film): ν=3502 (br.), 3049, 2958, 2879, 1722, 1713, 1460, 1452, 1356, 1313, 1281, 1165, 1080, 1036, 955 cm$^{-1}$ $^1$H-NMR of main diastereomer (270 MHz in CDCl$_3$): δ=0.50–0.70 (2H, m), 0.80–0.95 (4H, m), 1.10–1.30 (3H, m), 1.30–2.65 (17H, m), 2.75–3.20 (3H, m), 3.52 (1H, m), 5.85–6.00 (2H, m).

Synthesis Example 10

Synthesis of 2-ethyl-2-exo-norbornyl 3-hydroxy-3-(8-tetracyclo[4.4.0.1$^{2,5}$.1$^{7,10}$]dodecen-3-yl) propionate (Monomer 10)

The procedure of Synthesis Example 8 was repeated except that 2-ethyl-2-exo-norbornyl acetate was used instead of tert-butyl acetate. There was obtained 2-ethyl-2-exo-norbornyl 3-hydroxy-3-(8-tetracyclo[4.4.0.1$^{2,5}$.1$^{7,10}$]dodecen-3-yl)propionate. Yield 90%.

IR (KBr): ν=3483, 3049, 2962, 2879, 1711, 1466, 1456, 1358, 1313, 1170, 1132, 1038, 972, 953 cm$^{-1}$ $^1$H-NMR of main diastereomer (270 MHz in CDCl$_3$): δ=0.50–0.70 (2H, m), 0.75–0.95 (4H, m), 1.00–2.65 (22H, m), 2.70–2.90 (2H, m), 3.01 (1H, m), 3.52 (1H, m), 5.85–5.95 (2H, m).

Synthesis Example 11

Synthesis of 1-ethylcyclopentyl 3-hydroxy-3-(8-tetracyclo-[4.4.0.1$^{2,5}$.1$^{7,10}$]dodecen-3-yl)butyrate (Monomer 11)

The procedure of Synthesis Example 9 was repeated except that 8-acetyl-3-tetracyclo[4.4.0.1$^{2,5}$.1$^{7,10}$]dodecene was used instead of 8-tetracyclo[4.4.0.1$^{2,5}$.1$^{7,10}$]dodecene-3-carbaldehyde. There was obtained 1-ethylcyclopentyl 3-hydroxy-3-(8-tetracyclo[4.4.0.1$^{2,5}$.1$^{7,10}$]dodecen-3-yl)butyrate. Yield 92%.

IR (thin film): ν=3502 (br.), 3049, 2958, 2877, 1705, 1713, 1460, 1373, 1354, 1336, 1205, 1169, 958 cm$^{-1}$ $^1$H-NMR of main diastereomer (270 MHz in CDCl$_3$): δ=0.79 (1H, m), 0.87 (3H, t, J=7.3 Hz), 1.10–1.50 {(8H, m) including 1.17 (3H, s)}, 1.50–1.80 (6H, m), 1.85–2.25 (9H, m), 2.26 (1H, d, J=15.1 Hz), 2.41 (1H, d, J=15.1 Hz), 2.75–2.85 (2H, m), 3.66 (1H, m), 5.90–5.95 (2H, m).

Synthesis Example 12

Synthesis of 2-ethyl-2-exo-norbornyl 3-hydroxy-3-(8-tetracyclo[4.4.0.1$^{2,5}$.1$^{7,10}$]dodecen-3-yl)butyrate (Monomer 12)

The procedure of Synthesis Example 11 was repeated except that 2-ethyl-2-exo-norbornyl acetate was used instead of 1-ethylcyclopentyl acetate. There was obtained 2-ethyl-2-exo-norbornyl 3-hydroxy-3-(8-tetracyclo-[4.4.0.1$^{2,5}$.1$^{7,10}$]dodecen-3-yl)butyrate. Yield 90%.

IR (thin film): ν=3500 (br.), 3049, 2962, 2873, 1705, 1458, 1373, 1354, 1331, 1248, 1201, 1173, 1132, 1107, 951 cm$^{-1}$ $^1$H-NMR of main diastereomer (270 MHz in CDCl$_3$): δ=0.80 (1H, m), 0.82 (3H, t, J=7.3 Hz), 1.00–2.30 {(25H, m) including 1.18 (3H, s), 2.26 (1H, d, J=15.1 Hz)}, 2.41 (1H, d, J=15.1 Hz), 2.53 (1H, m), 2.75–2.85 (2H, m), 3.73 (1H, m), 5.85–5.95 (2H, m).

Synthesis Example 13

Synthesis of 2-ethyl-2-exo-norbornyl 3-hydroxy-4-(5-norbornen-2-yl)butyrate (Monomer 13)

By following the procedure of Synthesis Example 2 except that 2-(5-norbornen-2-yl)acetaldehyde was used instead of 5-norbornene-2-carbaldehyde, there was obtained 2-ethyl-2-exo-norbornyl 3-hydroxy-4-(5-norbornen-2-yl)-butyrate. Yield 94%.

IR (thin film): ν=3467 (br.), 3057, 2964, 2870, 1724, 1457, 1441, 1333, 1265, 1190, 1171, 1132, 1107, 955 cm$^{-1}$ $^1$H-NMR of main diastereomer (270 MHz in CDCl$_3$): δ=0.53 (1H, m), 0.82 (3H, t, J=7.3 Hz), 1.00–2.05 (14H, m), 2.15–2.50 (5H, m), 2.53 (1H, m), 2.70–2.85 (2H, m), 3.04 (1H, m), 3.95 (1H, m), 5.91 (1H, m), 6.11 (1H, m).

Synthesis Example 14

Synthesis of 2-ethyl-2-exo-norbornyl 3-hydroxy-3-methyl-5-(5-norbornen-2-yl)valerate (Monomer 14)

By following the procedure of Synthesis Example 2 except that 4-(5-norbornen-2-yl)butanone was used instead of 5-norbornene-2-carbaldehyde, there was obtained 2-ethyl-2-exo-norbornyl 3-hydroxy-3-methyl-5-(5-norbornen-2-yl)valerate. Yield 92%.

IR (thin film): ν=3502 (br.), 3057, 2966, 2937, 2870, 1705, 1458, 1441, 1348, 1331, 1200, 1173, 1132, 1107, 951 cm$^{-1}$ $^1$H-NMR of main diastereomer (300 MHz in CDCl$_3$): δ=0.48 (1H, m), 0.82 (3H, t, J=7.6 Hz), 1.00–2.05 {(20H, m) including 1.17 (3H, s)}, 2.15–2.30 (2H, m), 2.32 (1H, d, J=14.9 Hz), 2.39 (1H, d, J=14.9 Hz), 2.53 (1H, m), 2.70–2.80 (2H, m), 3.80 (1H, t, J=10.8 Hz), 5.90 (1H, m), 6.10 (1H, m).

Synthesis Example 15

Synthesis of 1-ethylcyclohexyl 3-hydroxy-3-methyl-4-(5-norbornen-2-yl)butyrate (Monomer 15)

The procedure of Synthesis Example 1 was repeated except that 1-ethylcyclohexyl acetate was used instead of 1-ethylcyclopentyl acetate, and 3-(5-norbornen-2-yl)acetone was used instead of 5-norbornene-2-carbaldehyde. There was obtained 1-ethylcyclohexyl 3-hydroxy-3-methyl-4-(5-norbornen-2-yl)butyrate. Yield 92%.

Synthesis Example 16

Synthesis of 8-ethyl-8-exo-tricyclo[5.2.1.0$^{2,6}$]decanyl 3-hydroxy-5-(5-norbornen-2-yl)valerate (Monomer 16)

The procedure of Synthesis Example 1 was repeated except that 8-ethyl-8-exo-tricyclo[5.2.1.0$^{2,6}$]decanyl acetate was used instead of 1-ethylcyclopentyl acetate, and 3-(5-norbornen-2-yl)propionaldehyde was used instead of 5-norbornene-2-carbaldehyde. There was obtained 8-ethyl-8-exo-tricyclo[5.2.1.0$^{2,6}$]decanyl 3-hydroxy-5-(5-norbornen-2-yl)valerate. Yield 93%.

Synthesis Example 17

Synthesis of 2-ethyl-2-adamantyl 3-hydroxy-5-(5-norbornen-2-yl)valerate (Monomer 17)

The procedure of Synthesis Example 16 was repeated except that 2-ethyl-2-adamantyl acetate was used instead of 8-ethyl-8-exo-tricyclo[5.2.1.0$^{2,6}$]decanyl acetate. There was obtained 2-ethyl-2-adamantyl 3-hydroxy-5-(5-norbornen-2-yl)valerate. Yield 92%.

Synthesis Example 18

Synthesis of 2-(1-adamantyl)-2-propyl 3-hydroxy-6-(5-norbornen-2-yl)hexanoate (Monomer 18)

The procedure of Synthesis Example 1 was repeated except that 2-(1-adamantyl)-2-propyl acetate was used instead of 1-ethylcyclopentyl acetate, and 4-(5-norbornen-2-yl)butyrylaldehyde was used instead of 5-norbornene-2-carbaldehyde. There was obtained 2-(1-adamantyl)-2-propyl 3-hydroxy-6-(5-norbornen-2-yl)hexanoate. Yield 93%.

Synthesis Example 19

Synthesis of 2-(2-norbornyl)-2-propyl 3-hydroxy-6-(5-norbornen-2-yl)hexanoate (Monomer 19)

The procedure of Synthesis Example 18 was repeated except that 2-(2-norbornyl)-2-propyl acetate was used instead of 1-ethylcyclopentyl acetate. There was obtained 2-(2-norbornyl)-2-propyl 3-hydroxy-6-(5-norbornen-2-yl)hexanoate. Yield 92%.

Synthesis Example 20

Synthesis of 3-ethyl-3-pentyl 3-hydroxy-3-methyl-6-(5-norbornen-2-yl)hexanoate (Monomer 20)

The procedure of Synthesis Example 1 was repeated except that 3-ethyl-3-pentyl acetate was used instead of 1-ethylcyclopentyl acetate, and 5-(5-norbornen-2-yl)-2-pentanone was used instead of 5-norbornene-2-carbaldehyde. There was obtained 3-ethyl-3-pentyl 3-hydroxy-3-methyl-6-(5-norbornen-2-yl)hexanoate. Yield 91%.

The structural formulas of Monomers 1 to 20 are shown below.

Monomer 1

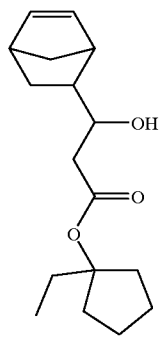

Monomer 2

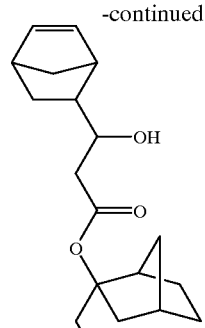

Monomer 3

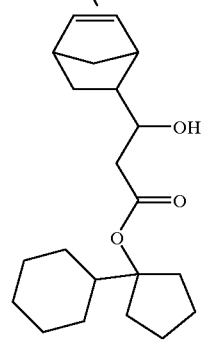

Monomer 4

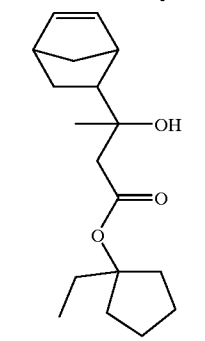

Monomer 5

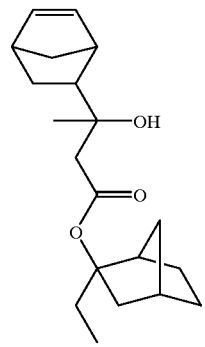

Monomer 6

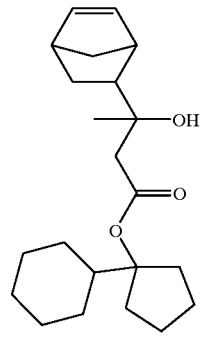

-continued
Monomer 7
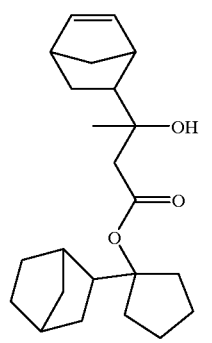
Monomer 8
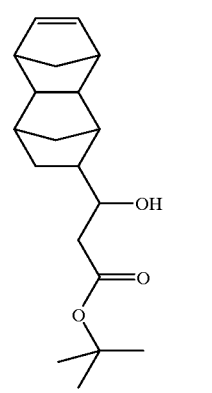
Monomer 9
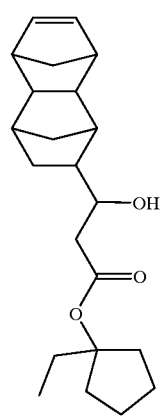
Monomer 10
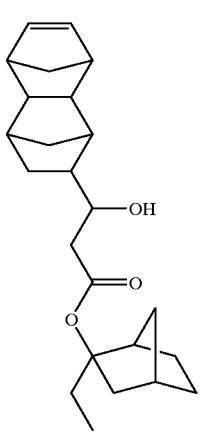
Monomer 11
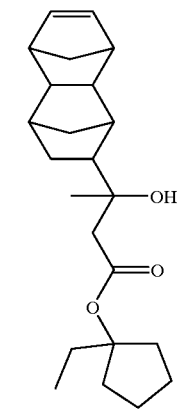
Monomer 12
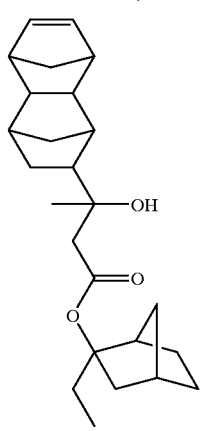
Monomer 13
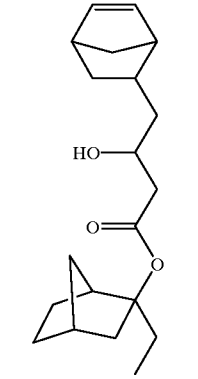
Monomer 14
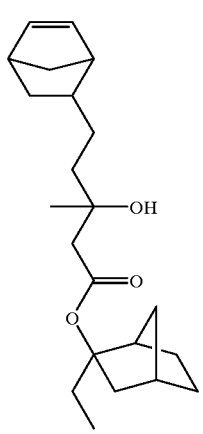

-continued
Monomer 15
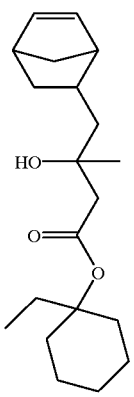
Monomer 16
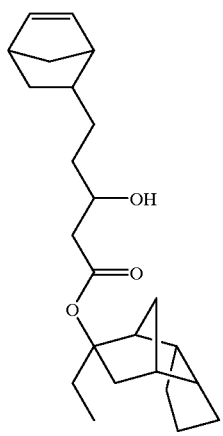
Monomer 17
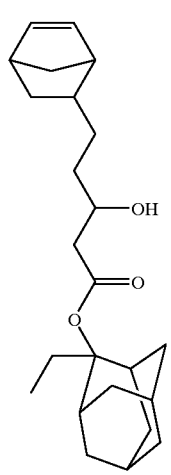
-continued
Monomer 18
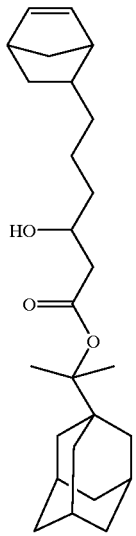
Monomer 19
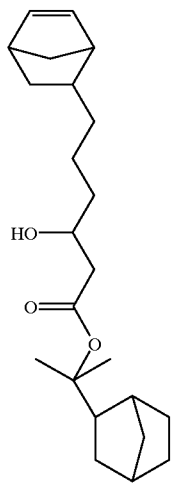
Monomer 20
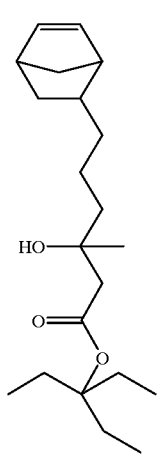

Reference Example

Polymers were synthesized using the ester compounds obtained in the above Synthesis Examples. Using the polymers as a base resin, resist compositions were prepared, which were examined for reactivity.

Polymerization reaction was effected between Monomer 1 and maleic anhydride using the initiator V65 (by Wako Junyaku K.K.), yielding an alternating copolymer of 1-ethylcyclopentyl 3-hydroxy-3-(5-norbornen-2-yl)-propionate/maleic anhydride.

A resist composition was prepared by blending 80 parts by weight of the above copolymer as a base resin, 1.0 part by weight of triphenylsulfonium trifluoromethanesulfonate as a photoacid generator, 480 parts by weight of propylene glycol monomethyl ether acetate as a solvent, and 0.08 part by weight of tributylamine. The composition was spin coated on a silicon wafer and heat treated at 110° C. for 90 seconds, forming a resist film of 500 nm thick. The resist film was exposed to ArF excimer laser light, heat treated at 110° C. for 90 seconds, and developed by immersing in a 2.35% tetramethylammonium hydroxide aqueous solution for 60 seconds. The dose of exposure (Eth) which allowed the resist film to be fully dissolved was determined to be 8.0 mJ/cm².

Comparative Reference Example

For comparison purposes, a similar resist composition was prepared using an alternating copolymer of tert-butyl 5-norbornene-2-carboxylate/maleic anhydride. The composition was examined by the same exposure test, finding a dose Eth of 12.5 mJ/cm².

It was confirmed that polymers resulting from the inventive ester compounds have very high reactivity as compared with prior art polymers.

Japanese Patent Application No. 2000-131177 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. An ester compound of the following general formula (1):

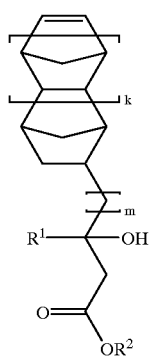

(1)

wherein $R^1$ is hydrogen or a straight, branched or cyclic alkyl group of 1 to 6 carbon atoms, $R^2$ is an acid labile group, represented by

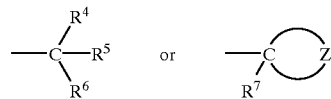

wherein $R^4$ to $R^7$ are independently selected from straight, branched or cyclic alkyl groups of 1 to 15 carbon atoms, the sum of carbon atoms in $R^4$, $R^5$ and $R^6$ is at least 5 and at least one of $R^4$ to $R^6$ is a cyclic alkyl group of 3 to 15 carbon atoms, and Z is a divalent hydrocarbon group of 4 to 15 carbon atoms which form a ring with the carbon atom to which it is connected at opposite ends, k is 0 or 1, and m is an integer from 0 to 5.

2. The ester compound of claim 1 having the following general formula (2) or (3):

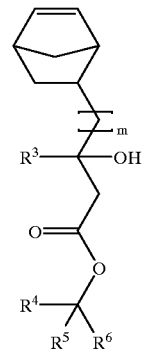

(2)

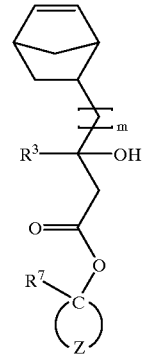

(3)

wherein m is as defined above, $R^3$ is hydrogen or methyl, $R^4$ to $R^7$ are independently selected from straight, branched or cyclic alkyl groups of 1 to 15 carbon atoms, the sum of carbon atoms in $R^4$, $R^5$ and $R^6$ is at least 5, and at least one of $R^4$ to $R^6$ is a cyclic alkyl group of 3 to 15 carbon atoms, and Z is a divalent hydrocarbon group of 4 to 15 carbon atoms which forms a ring with the carbon atom to which it is connected at opposite ends.

3. A method for preparing the ester compound of claim 1 or 2, comprising the step of effecting addition reaction of a metal enolate of acetate of the following formula (5) to a carbonyl compound of the following formula (4),

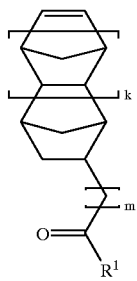

(4)

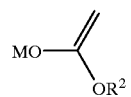

(5)

wherein k, m, $R^1$ and $R^2$ are as defined above, M is Li, Na, K or MgY, and Y is a halogen atom.

4. An ester compound according to claim 1, wherein the $R^1$ alkyl group is methyl, ethyl, propyl, isopropyl, butyl, isobutyl, sec-butyl, tert-butyl, tert-amyl, pentyl, hexyl, cyclopentyl, or cyclohexyl.

5. An ester compound according to claim 1, wherein m is an integer from 0 to 3.

6. An ester compound according to claim 2, wherein the straight, branched or cyclic alkyl groups of $R^4$ to $R^7$ include methyl, ethyl, propyl, isopropyl, butyl, isobutyl, sec-butyl, tert-butyl, tert-amyl, pentyl, hexyl, cyclopentyl, cyclohexyl, cyclopentylmethyl, cyclopentylethyl, cyclohexylmethyl, cyclohexylethyl, bicyclo[2.2.1]heptyl, bicyclo[2.2.2]octyl, bicyclo[3.3.1]nonyl, bicyclo[4.4.0]decanyl, tricyclo[5.2.1.0$^{2,6}$]decanyl, tetracyclo[4.4.0.1$^{2,5}$.1$^{7,10}$]dodecanyl or adamantyl.

7. An ester compound according to claim 2, wherein the rings that Z forms is cyclopentane cyclopentene, cyclohexane, cyclohexene, bicyclo[2.2.1]heptane, bicyclo[4.4.0]decane, tricyclo[5.2.1.0$^{2,6}$]decane, tetracyclo[4.4.0.1$^{2,5}$.1$^{7,10}$]-dodecane, or adamantane.

8. A method according to claim 3 including a step wherein a base acts on a corresponding acetate or a corresponding haloacetate to form the metal enolate.

9. A method according to claim 3, wherein the addition reaction is conducted at a reaction temperature of −80° C. to −30° C. and a reaction time of about ½ to about 3 hours.

10. A method according to claim 3, wherein the addition reaction is conducted at a reaction temperature of 20 to 80° C. and a reaction time of about 1 to about 20 hours.

11. A method of preparing a polymer comprising mixing the monomer of claim 1 with a solvent, adding a catalyst or polymerization initiator, and effecting polymerization reaction while optionally heating or cooling the reactants.

12. An ester compound of the following general formula (1):

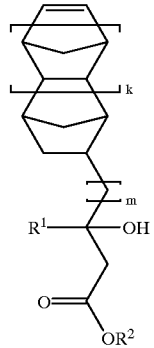

(1)

wherein $R^1$ is hydrogen or a straight, branched or cyclic alkyl group of 1 to 6 carbon atoms, $R^2$ is an acid labile group, represented by

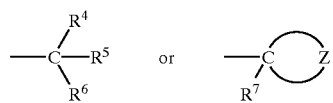

wherein $R^4$ to $R^7$ are independently selected from straight, branched or cyclic alkyl groups of 1 to 15 carbon atoms, the sum of carbon atoms in $R^4$, $R^5$ and $R^6$ is at least 5, and Z is a divalent hydrocarbon group of 4 to 15 carbon atoms which form a ring with the carbon atom to which it is connected at opposite ends, k is 0 or 1, and m is an integer from 0 to 5.

13. The ester compound of claim 12 having the following general formula (2) or (3):

(2)

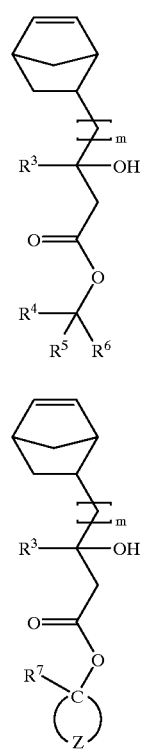

(3)

wherein m is as defined above, $R^3$ is hydrogen or methyl, $R^4$ to $R^7$ are independently selected from straight, branched or cyclic alkyl groups of 1 to 15 carbon atoms, the sum of carbon atoms in $R^4$, $R^5$ and $R^6$ is at least 5, and Z is a divalent hydrocarbon group of 4 to 15 carbon atoms which forms a ring with the carbon atom to which it is connected at opposite ends.

14. A method for preparing the ester compound of claim 1, comprising the step of effecting addition reaction of a metal enalote of acetate of the following formula (5) to a carbonyl compound of the following formula (4),

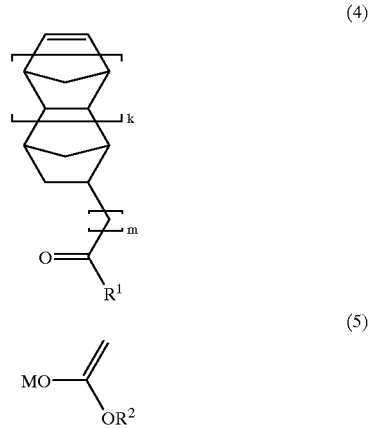

(4)

(5)

wherein k, m, $R^1$ and $R^2$ are as defined above, M is Li, Na, K, MgY, or ZnY and Y is a halogen atom.

* * * * *